United States Patent
Cleary et al.

(10) Patent No.: US 7,611,481 B2
(45) Date of Patent: Nov. 3, 2009

(54) TRANSDERMAL DELIVERY DEVICE

(75) Inventors: Gary W. Cleary, Los Altos Hills, CA (US); Steven R. Klemm, Grand Rapids, MI (US)

(73) Assignee: Corium International, Inc., Menlo Park, CA (US)

( * ) Notice: Subject to any disclaimer, the term of this patent is extended or adjusted under 35 U.S.C. 154(b) by 312 days.

(21) Appl. No.: 11/088,829

(22) Filed: Mar. 24, 2005

(65) Prior Publication Data

US 2005/0228340 A1 Oct. 13, 2005

Related U.S. Application Data

(60) Provisional application No. 60/555,841, filed on Mar. 24, 2004.

(51) Int. Cl.
*A61B 17/20* (2006.01)
(52) U.S. Cl. .............. 604/46; 604/27; 604/87; 604/289; 604/290; 604/310; 604/890.1
(58) Field of Classification Search .............. 604/890.1, 604/891.1, 892.1, 1–3, 19–22, 46–48, 502, 604/87, 93.01, 115, 180, 181, 183, 191, 239, 604/244, 272, 289, 306, 307, 308, 27, 310
See application file for complete search history.

(56) References Cited

U.S. PATENT DOCUMENTS

| | | | |
|---|---|---|---|
| 3,964,482 A * | 6/1976 | Gerstel et al. ............ | 604/890.1 |
| 4,117,841 A | 10/1978 | Perrotta et al. | |
| 4,402,696 A | 9/1983 | Gulko | |
| 4,460,368 A | 7/1984 | Allison et al. | |
| 4,460,370 A | 7/1984 | Allison et al. | |
| 4,556,441 A | 12/1985 | Faasse, Jr. | |
| 4,597,961 A | 7/1986 | Etscorn | |
| 4,743,249 A | 5/1988 | Loveland | |
| 4,812,305 A | 3/1989 | Vocal | |
| 4,904,475 A | 2/1990 | Gale et al. | |
| 5,051,259 A | 9/1991 | Olsen et al. | |
| 5,061,258 A * | 10/1991 | Martz ......................... | 604/307 |
| 5,160,315 A | 11/1992 | Heinecke et al. | |
| 5,244,677 A | 9/1993 | Kreckel et al. | |
| 5,250,023 A * | 10/1993 | Lee et al. ...................... | 604/20 |
| 5,308,625 A | 5/1994 | Wong et al. | |
| 5,330,452 A | 7/1994 | Zook | |
| 5,462,743 A | 10/1995 | Turner et al. | |
| 5,476,443 A * | 12/1995 | Cartmell et al. .............. | 602/58 |
| 5,503,843 A * | 4/1996 | Santus et al. ................. | 424/448 |
| 5,520,629 A | 5/1996 | Heinecke et al. | |
| 5,531,855 A | 7/1996 | Heinecke et al. | |
| 5,730,721 A | 3/1998 | Hyatt et al. | |

(Continued)

*Primary Examiner*—Nicholas D Lucchesi
*Assistant Examiner*—Quynh-Nhu H Vu
(74) *Attorney, Agent, or Firm*—Flavio M. Rose; Mintz, Levin, Cohn, Ferris, Glovsky and Popeo, PC

(57) ABSTRACT

A dermal, transdermal, mucosal or transmucosal delivery device includes a backing layer overlying an ingredient containing reservoir, and having a microprotrusion array attached thereto, a cover for the reservoir having at least one opening therethrough, an adhesive layer and a liner layer. Upon removal of the liner layer, the device may be placed over the desired area of the skin or mucosa and adhesively applied thereto allowing the ingredients to flow from the reservoir through the at least one opening to the skin or mucosa.

23 Claims, 8 Drawing Sheets

U.S. PATENT DOCUMENTS

| | | | |
|---|---|---|---|
| 5,738,642 A | 4/1998 | Heinecke et al. | |
| 5,756,117 A | 5/1998 | D'Angelo et al. | |
| 5,788,983 A | 8/1998 | Chien et al. | |
| 5,851,549 A | 12/1998 | Svec | |
| 5,932,240 A | 8/1999 | D'Angelo et al. | |
| 5,962,011 A | 10/1999 | DeVillez et al. | |
| 6,120,792 A | 9/2000 | Juni | |
| 6,156,336 A | 12/2000 | Bracht | |
| 6,169,224 B1 | 1/2001 | Heinecke et al. | |
| 6,183,770 B1 | 2/2001 | Muchin et al. | |
| 6,375,978 B1 | 4/2002 | Kleiner et al. | |
| 6,611,707 B1* | 8/2003 | Prausnitz et al. | 604/21 |
| 6,623,457 B1* | 9/2003 | Rosenberg | 604/191 |
| 6,652,478 B1 | 11/2003 | Gartstein et al. | |
| 6,656,147 B1* | 12/2003 | Gertsek et al. | 604/28 |
| 6,685,682 B1 | 2/2004 | Heinecke et al. | |
| 6,821,281 B2 | 11/2004 | Sherman et al. | |
| 2002/0016562 A1* | 2/2002 | Cormier et al. | 604/20 |
| 2002/0193729 A1* | 12/2002 | Cormier et al. | 604/46 |
| 2003/0166624 A1* | 9/2003 | Gale et al. | 514/171 |
| 2003/0187394 A1* | 10/2003 | Wilkinson et al. | 604/131 |
| 2005/0089554 A1* | 4/2005 | Cormier et al. | 424/448 |
| 2005/0163827 A1* | 7/2005 | Zech et al. | 424/448 |

* cited by examiner

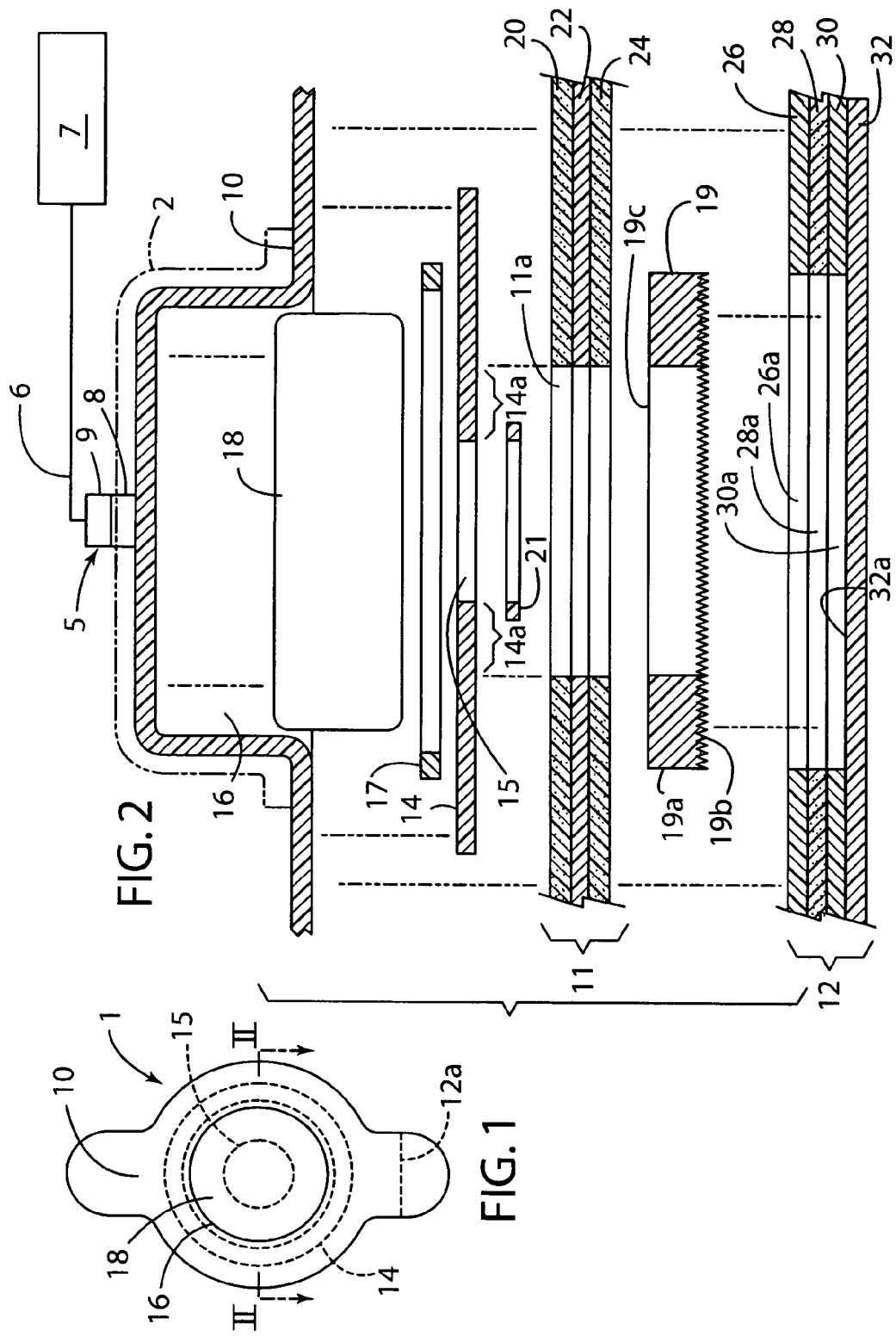

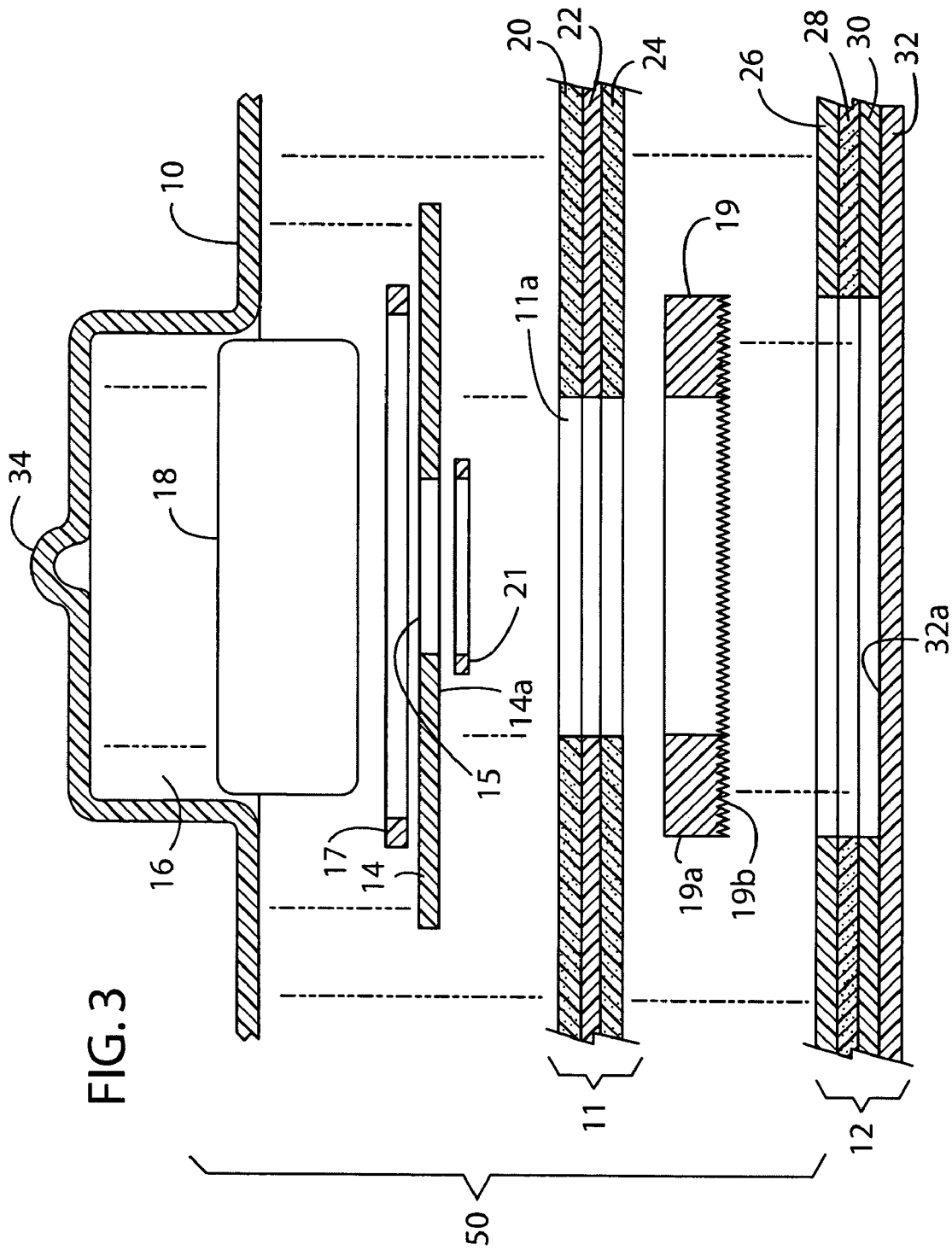

TRANSDERMAL DELIVERY DEVICE

CROSS-REFERENCE TO RELATED APPLICATIONS

This application claims the benefit of U.S. Provisional Application No. 60/555,841, filed on Mar. 24, 2004, the entire contents of which are hereby incorporated by reference.

BACKGROUND OF THE INVENTION

The concept of minimally invasive transdermal drug delivery systems has been developed over time to overcome, or at least provide an alternative to, the drawbacks of conventional metal needle drug delivery. These minimally invasive transdermal mucosal drug delivery systems have been designed to allow drugs to pass through the stratum corneum layer of the skin and the epithelial cells of the mucosa thereby enabling drugs to bypass this skin and mucosa barrier and deliver drugs into the microvascularization of the dermis and mucosa or their lower tissues and potentially into systemic circulation.

The present invention relates to such transdermal drug delivery devices. Such devices typically comprise a patch containing a drug to be delivered. The patch typically includes an adhesive layer for adherence to a patient's skin. The drug may be present as a liquid in a reservoir, or in a gel, or may be incorporated into the adhesive layer of the patch. The patch is applied to a person's skin and the drug passes through the skin into the patient's system as well as the dermal, mucosal and transmucosal.

In some drug delivery systems, one removes the stratum corneum layer of the skin in preparation of topical administration of a drug. Removal of the stratum corneum layer is typically done by scrapping the skin with a mechanical device or by repeatedly applying a tape strip to the surface of the skin and then removing the tape to remove the stratum corneum layer of the skin. Both of these methods of removing the stratum corneum layer of the skin are cumbersome and uncontrolled methods utilized in preparation of topical administration of a drug.

Transdermal delivery devices have also been developed which include hollow microneedles which are forced through the stratum corneum. U.S. Pat. No. 6,611,707 B1 to Prausnitz et al. discloses a microneedle drug delivery device having one or more drug reservoirs positioned over a housing which includes an array of hollow microneedles, with a seal located therebetween. An adhesive layer is applied in-between the microneedles at their base, or to an attachment collar or tabs adjacent the microneedles, to facilitate adherence of the device to the skin. The delivery of drug from a reservoir is initiated by removing or breaking the seal and applying a force, such as by pressing the top of the reservoir, to cause the reservoir contents to flow out through the microneedles. The microneedle device includes a feedback means so that the user can (1) determine whether delivery has been initiated, and/or (2) confirm that the reservoir has been emptied. Representative feedback means include a sound, a color change indicator, or a change in the shape of a deformable reservoir. U.S. Pat. No. 6,656,147 to Gertsek is similar to Prausnitz U.S. Pat. No. 6,611,707, but has a housing which forms a collar extending away from the microprotrusion array. A pressure sensitive adhesive is applied to the underside of the collar so that the device is adhered to the skin.

U.S. Pat. No. 6,821,281 to Sherman et al. discloses a transdermal delivery device in which a reservoir is positioned above an array of microprotrusions which are not hollow, but which may include grooves. The microprotrusions are used to scrap skin cells from the skin when the device is moved in at least one direction. Medication forced out of the reservoir and flows down between the array of microprotrusions and into and through the patient's skin.

All of the above microneedle or microprotrusion array devices are relatively bulky and/or rigid devices employing some type of housing for the microneedle or microprotrusion array, and for the ingredient reservoir. The housing is typically made of a plastic material. U.S. Pat. No. 6,656,147 to Gertsek suggests a housing or bladder made of a flexible plastic or rubber like material.

As used herein, "microprotrusion" will be used as a generic term, encompassing microneedles as well as other types of small abrading protrusions. The "micro" portion of this term is usually understood to mean something so small that it can only be seen with a microscope. However, in this art, the micro portion of the term is understood to mean relatively small protrusions which often are typically at least sufficiently large to be seen with the naked eye. As used herein, "transdermal" will be used as a generic term encompassing dermal, mucosa and transmucosal as well.

SUMMARY OF THE INVENTION

In one aspect of the present invention, a microneedle or microprotrusion array is incorporated into a film type of ingredient delivery device. A backing layer of film overlying an ingredient reservoir includes a microprotrusion array attached thereto. A release liner film overlies the backing layer and the microprotrusion array.

These and other objects, advantages and features of the invention will be more fully understood and appreciated by reference to the written specification and appended drawings.

BRIEF DESCRIPTION OF THE DRAWINGS

FIG. 1 is a top plan view of the device of the preferred embodiment;

FIG. 2 is an exploded cross-sectional view of the principle subassemblies of the device of the preferred embodiment;

FIG. 3 is an exploded cross-sectional view of the principle subassemblies of the device of a second preferred embodiment;

Figure 4:
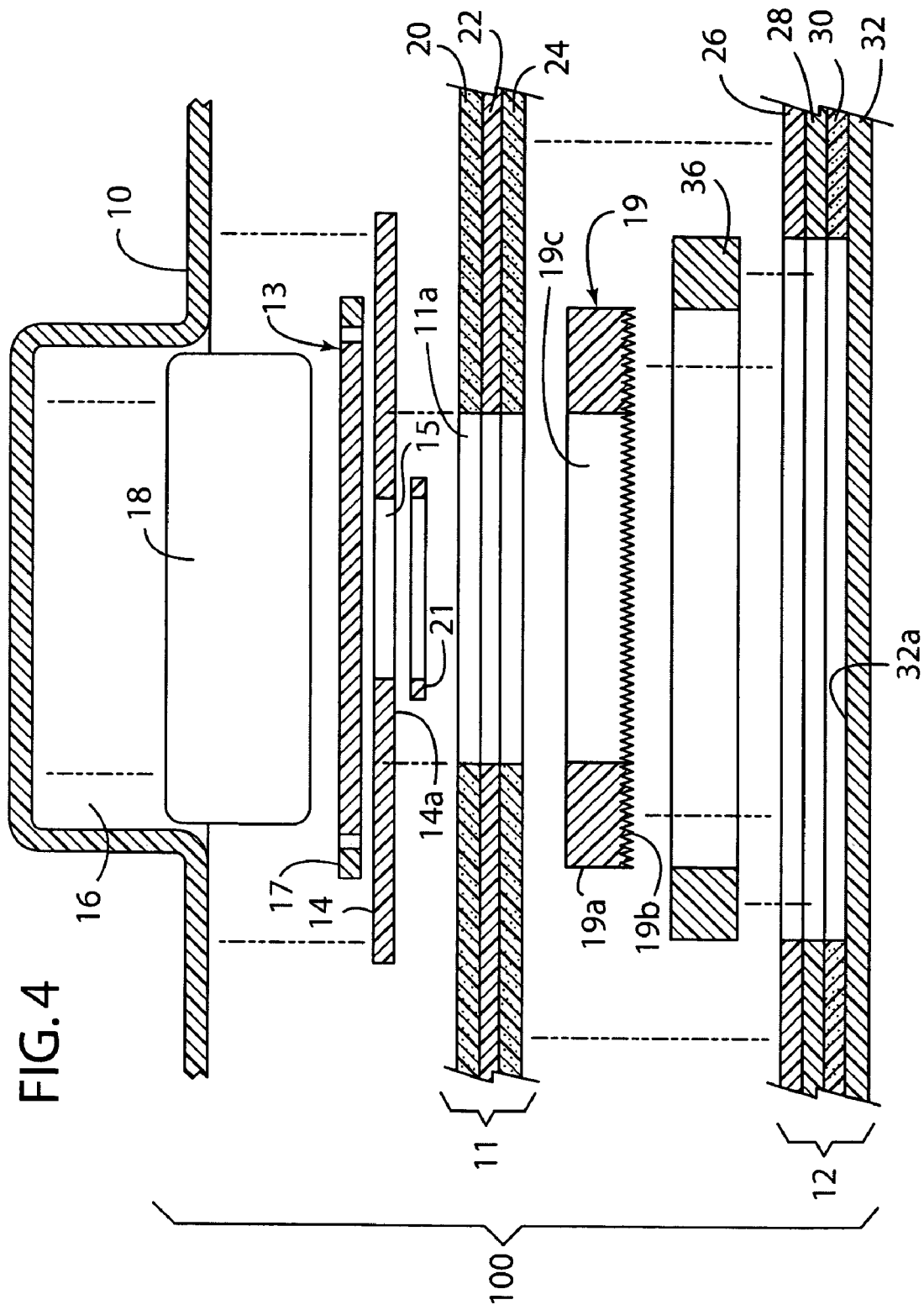
FIG. 4 is an exploded cross-sectional view of the principle subassemblies of the device of a third preferred embodiment.

It will be appreciated that the thicknesses and shapes for the various layers have been exaggerated in the drawings to facilitate understanding of the device. The drawings are not "to scale."

DETAILED DESCRIPTION OF PREFERRED EMBODIMENTS

Basic Reservoir System

In the preferred embodiment, device 1 comprises a backing layer (sometimes referred to as a base or backing member) 10 having a cavity or reservoir 16 overlying an ingredient reservoir 18 (FIGS. 1, 2, 3 and 4). A retaining ring or cover 14 having an opening 15 therein is sealed via a first ring-like seal 17 to backing member 10 around the periphery of reservoir 18. Seal 17 is made of a material that is not subject to degradation, permeation or solubilization by ingredients to be contained in reservoir 18. Seal 17 may be omitted according to other aspects of the invention. If seal 17 is not utilized, cover 14 is heat sealed or otherwise directly to backing. Adhesive layer 11 is adhered to backing member 10 and serves to adhere the device to a patient's skin or mucosa. Adhesive layer 11 may cover a portion of cover 14, but includes an opening 11a such that adhesive layer 11 does not cover opening 15. Adhesive layer 11 preferably leaves a ring-like edge portion of the surface of cover 14 exposed in the area surrounding opening 15, the area being referred to herein as cover sealing surface 14a. A microprotrusion member or layer 19 is disposed between the adhesive layer 11 and a liner 12. The term microprotrusion as used herein is used generically to describe any type of protruding implement which is capable of penetrating a patient's skin. Thus, the microprotrusions might be solid needles, hollow needles, solid protrusions or other such configurations, hollow protrusions or other such configurations, grooved protrusions or any other configuration capable of penetrating the patient's skin.

Turning to FIG. 1 which is a plan view of the device of the present invention, there is an opening 15 in cover 14 for release of the medication to the patient's skin from the reservoir 18 that may contain a thin absorbable ingredient containing woven or non-woven layer, which, in turn, is contained within the cover 14 that is sealed to backing layer 10. A kiss cut line 12a is present in release liner 12 to aid in removing the disposable release liner 12. While device 1 may be any shape, FIG. 1 shows the preferred shape of the present invention.

Port Fitting Design

Device 1 may optionally include a fitting 5 that is connected to a tube 6. Fitting 5 may be a Luer Lock fitting having a male fitting 8 that is releasably, yet sealingly connected to a female fitting 9. A pump 7 may be utilized to pressurize reservoir 18 to promote transdermal delivery of the ingredients in reservoir 18. Pump 7 may comprise a syringe, an I.V. bag that is elevated above reservoir 18, or a mechanical pump that is manually powered. Alternately pump 7 may comprise a powered pump that is operably connected to a controller (not shown) to provide pressure according to a predetermined program or schedule. Also an injectable sealing layer (not shown) may also be used in place of the Luer Lock fitting. A hollow needle (not show) that is attached to tube 6 is used to pierce the resealable membrane to thereby provide a fluid connection between pump 7 and reservoir 18.

The microprotrusion layer 19 includes a base 19a and a plurality of protrusions 19b projecting from base 19a. Microprotrusion layer 19 also includes at least one opening 19c therethrough that corresponds with the opening 11a in adhesive layer 11 such that the reservoir ingredients may flow into and through these openings 11a and 19c when the device 1 is in use. Liner 12 covers at least opening 15 and sealing surface 14a of cover 14, and is sealed to sealing surface by a ring-like second seal 21. Second seal 21 is made of a material that is not subject to degradation by any of the ingredients in the reservoir. Preferably, liner 12 comprises the release liner for the device 1, and therefore covers not only opening 15 and sealing surface 14, but also releasably covers the at least one opening 19c in microprotrusion layer 19 and opening 11a adhesive layer 11. As described in more detail below, when device 1 is used, release liner 12 is removed, thereby exposing opening 15. Device 1 is then applied and adhered to the patient's skin or mucosa via adhesive layer 11. During the application process, the microprotrusion layer 19 is depressed into a patient's skin or mucosa to a desired depth with reservoir 16 and cover opening 15 positioned over the area to which ingredients are to be delivered.

Reservoir Shell Covering

The preferred embodiment device may also include a shell 2 (FIG. 2) covering the exterior of reservoir overlying portion 16. The shell 2 of the device should be impermeable or impervious to the liquid being delivered to the treatment site, in order to prevent loss by evaporation or wetting. The shell 2 may also protect the active ingredient and/or liquid against radiant energy sources such as ultraviolet and visible light. The shell 2 can be either dimensionally stable or dimensionally non-stable, preferably dimensionally non-stable. A dimensionally non-stable shell is not capable of withstanding a compressive force of one psi or less, i.e. will at least partially crush or collapse. Suitable materials for the shell 2 can include but are not limited to ceramics, metals such as titanium, aluminum or steel, plastics such as polyolefins, barex, styrene, polyesters, polyacrylics, vinylpolymers, polyamides, polyfluorocarbons, polyimides, polylactams, polyaramides, polycarbonates, polysulfones, polyethylene, polypropylene, nylon, polyvinyl chloride, polyvinylidiene chloride or combinations or composites thereof. It will be appreciated that the shell could replace the reservoir overlying portion 16 of the film of material comprising backing layer 10. In that case, the reader should consider the shell to be a part of backing layer 10 for purposes of this discussion. The shell would then be the portion of backing layer 10 defining overlying reservoir portion 16 for containing the ingredients to be delivered. The reservoir overlying portion 16 can be either dimensionally stable or dimensionally non-stable, as discussed above. The first heat seal 17 around reservoir overlying portion 16 should also be resistant to permeation, disintegration or degradation e.g., dissolving by the ingredients and actives contained herein.

The size or diameter of opening 15 may vary, as a function of the speed with which one wants to deliver active ingredients, or the total amount of active ingredient one wants to deliver from reservoir 16. Depending on intended use, the diameter of opening 15 may range from 0.05 to 5.0 inches. The larger openings may require the use of hydrogel in the reservoir 18, so the ingredient solution does not immediately run out of reservoir area 16 when liner 12 is removed. In the preferred embodiment as shown in FIG. 2, the diameter of opening 15 is approximately 0.125 inches. Also, cover 14 may have a plurality of openings 15. The geometry of opening 15 may be in the form of many shapes, i.e., round, rectangular, elliptical, square, etc.

Reservoir Layer

Ingredients may be contained within reservoir 18 in any of a variety of ways. For example, ingredient reservoir 18 can simply be in liquid or gel matrix form within overlying cavity or reservoir 16. The ingredients may be contained in a pad of hydrogel material, which basically comprises a gel matrix containing ingredients to be delivered through opening 15. Alternatively, ingredients may be contained in a woven or non-woven absorbable material reservoir pad 18 located beneath overlying reservoir 16, made of, for example, 5.0 mil STRATEX® 90% polypropylene/10% non-woven rayon. Other suitable materials for the absorbable woven or non-woven material include any non-dimensionally stable materials, such as woven polyester cloth, bonded nylon fibers, cotton gauze, fiberglass, polyester fibers and cotton fibers. This material may partially or completely contain the ingredient or ingredients to be delivered to the user's skin or mucosa. Also, the size and shape of opening 15 may be varied depending upon the requirements of a particular application. Also, a plurality of openings 15 may be utilized. If the device 1 is to be used on a skin surface that is generally vertical for substantial periods of time, opening 15 may be positioned off center, and an arrow or other indicia on backing 10 may be provided so a user can apply the device in an upright orientation. In this way, the opening 15 can be positioned at the bottom of the cavity 18 to ensure that the ingredients flow from reservoir 18 and through opening 15.

Ingredients Contained in Reservoir

The term ingredient or ingredients as used herein refers to all ingredients contained within ingredient reservoir 18, and not only to those of the ingredients which are to be delivered to or through the user's skin or mucosa. The latter may be referred to as "active" ingredients in the broadest sense. However, the term "active" ingredient is not intended to limit the ingredients to be delivered to drugs, since other types of ingredients may be delivered for purposes other than to serve as a drug.

Optionally, a rate controlling membrane layer 13 may be disposed between any of the layers of device 1 (FIG. 4). Rate controlling layer 13 is preferably disposed either between backing layer 10 and cover 14 or between cover 14 and adhesive layer 11. In FIG. 4, rate controlling membrane 13 is located between base layer 10 and cover 14. The rate controlling membrane may be a film of dense, microporous or pourous material.

Figure 5:
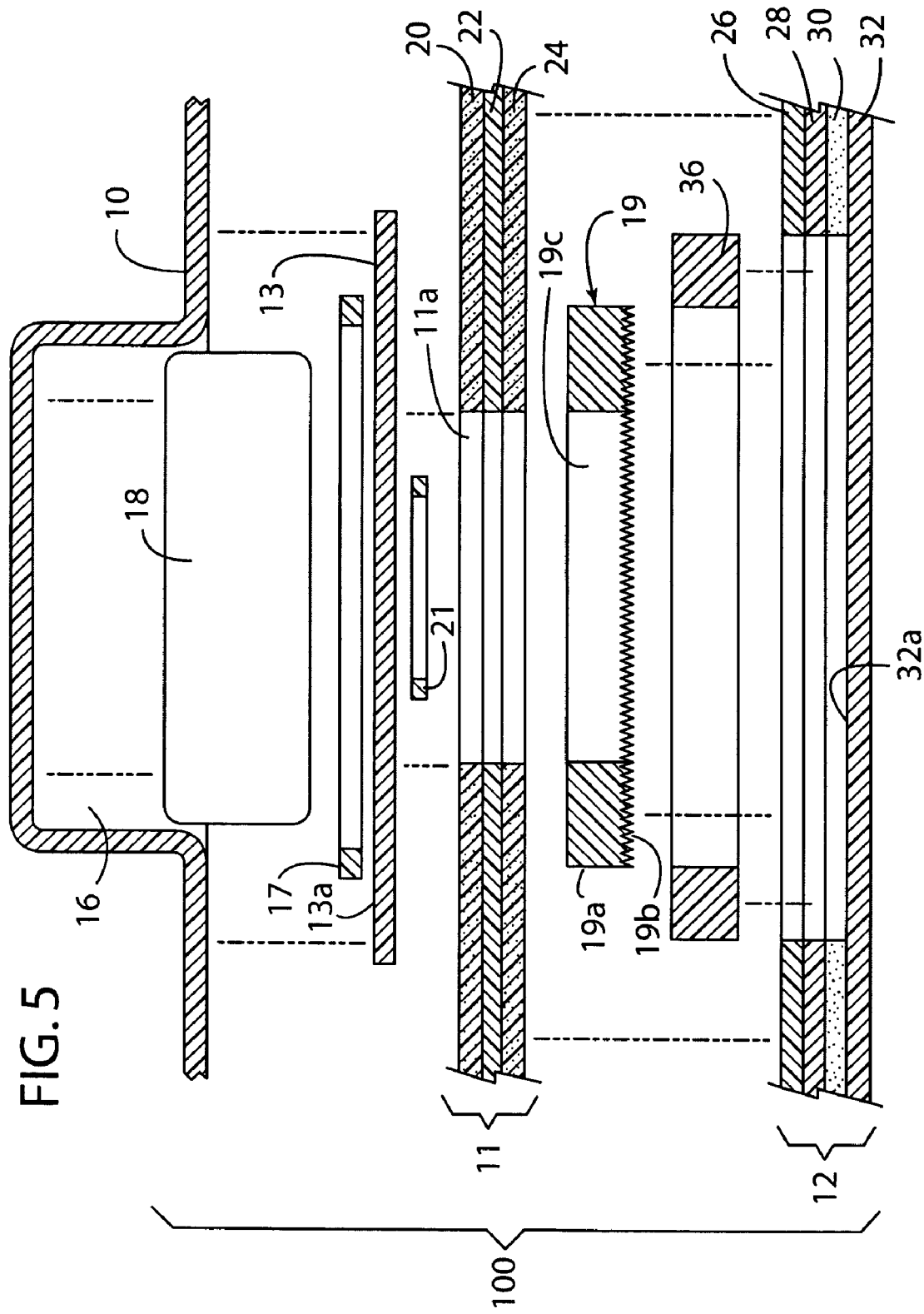
FIG. 5 is an exploded cross-sectional view of the principle subassemblies of the device of a fourth preferred embodiment.

Alternatively, cover 14 could be replaced entirely with a rate controlling membrane 13, as shown in FIG. 5, having no opening, such as opening 15 in cover 14. The rate controlling layer may include microporous openings that control the rate of passage of the reservoir containing ingredients from the reservoir 18 to the skin or mucosa. When rate controlling membrane 13 is utilized in place of cover 14, the exposed inner surface portion 32a of outer protective layer 32 is sealed to sealing surface 13a of rate controlling membrane 13 by a ring-like second seal 21 which is made of a material that does not degrade become permeable or solubilized when exposed to any of the ingredients contained in reservoir 18.

Backing Layer

Backing layer or base member 10 is made of a relatively hard polymer material, or a relatively soft polymer, such as a polyethylene terephthalate (P.E.T.) or polyvinylchloride (P.V.C.) material which is substantially impermeable to ingredients contained in reservoir 18. One example of a suitable material is 3.0 mil, 3M® 9722 polyethylene film. Base member 10 is thermoformed to form reservoir 16. Backing layer or base member 10 may be from about ½ mil to about 5 mils thick, preferably from about 1 mil to about 4 mils thick and most preferably about 3 mils thick. Retaining ring or cover 14 is also made of a material which is substantially impermeable to ingredients contained in reservoir 18, for example, 4.0 mil ROLLPRINT® polyethylene film that forms a reservoir 16. Preferably, the thickness of cover 14 may be from about 1 mil to about 10 mils thick, preferably from about 2 mils to about 8 mils thick and most preferably from about 3 mils to 6 mils thick.

Skin or Mucosa Adhesive Layer

Adhesive layer 11 is preferably a composite of three different layers (FIGS. 2, 3 and 4). Adhesive layer 11 is typically a composite of the following layers: first or upper adhesive layer 20, made of, for example, a 1.0 mil, NATIONAL STARCH 80-1197™ acrylic adhesive; barrier layer 22, made of, for example, a layer of 0.5 mil, PET film; and second or lower adhesive layer 24, made of, for example, 3.0 mil, NATIONAL STARCH 80-1197™ acrylic adhesive that comes into contact with the patient's skin. Adhesive layer 11 preferably has a thickness of from about 1 mil to about 10 mils, more preferably from about 2 mils to about 8 mils and most preferably from about 4 mils to about 6 mils. First or upper adhesive layer 20 and second or lower adhesive layer 24 each preferably have a thickness of from about ½ mil to about 5 mils, whereas barrier layer 22 preferably has a thickness of from about ½ mil to about 7 mils. The second or lower adhesive layer thickness may vary depending on the size of the transdermal device, the length of desired use, and the aggressiveness of the adhesive.

Other suitable materials for attaching the device 1 to the skin or mucosa may include waterproof tape or other materials that have an adhesive underside. A pressure sensitive adhesive or a combination of pressure sensitive adhesives are preferred. The adhesive may be resistant to permeation and/or dissolution by the ingredients in reservoir 18, but this is not essential in view of the first seals 17 and second seals 21 discussed above. Other suitable adhesives may include but are not limited to the following: A) Solvent-based acrylic adhesives such as: Monsanto GMS 737, trademark of Monsanto Corporation, St. Louis, Mo.; National Starch Durotak 72-9720 and 80-1197, trademark of National Starch & Chemical Corp., Bridgewater, N.J.; Ashland's AROSET 11 13-AD-40 and 1085-A-45, trademark of Ashland Oil Co., Ashland, Ky.; B) Solvent-based rubber adhesives such as: National Starch 36-6172; C. Acrylic emulsion adhesives such as: Monsanto GME 2397 Rohm & Haas N580, trademark of Rohm & Haas Co., Philadelphia, Pa.; Unocal 76 RES 9646, trademark of Unocal Corp., Los Angeles, Calif.; and Ashland's AROSET 2022-W-50; and C) Adhesive Transfer Tapes such as: 3M F-9465 PC, trademark of 2M Co., St. Paul, Minn. Avery-Denison MED 1116, trademark of Avery Dennison Corp., Pasadena, Calif.; ARCare 7530, trademark of Adhesive Research Inc., Glen Rock, Pa.; and RX230U, trademark of Coating Science Inc., Bloomfield, Conn.

The upper and lower adhesive layers 20 and 24 are both adhered to the intermediate barrier layer 22. Adhesive layer 20, in turn, is adhered to backing member 10, and also partially to cover 14, but does not extend beyond and over the sealing surface 14a of cover 14. Adhesive layer 11 may be any shape, however, ring-shaped is preferable.

Microprotrusion Layer

A microprotrusion layer 19 is disposed between the adhesive layer 11 and liner 12. Microprotrusion layer 19 includes a base layer 19a adjacent microprotrusions 19b. The microprotrusion layer 19 includes at least one opening 19c therein that corresponds with the opening in adhesive layer 11 such that the reservoir-containing ingredients may flow through these openings when the device 1 is in use. The microprotrusion layer side adjacent liner 12 contains microprotrusions 19b that project from the microprotrusion layer 19. As noted above, microprotrusions 19b may contain one or more channels or bores extending along an internal longitudinal axis of the microprotrusion. However, microprotrusions 19b may also be boreless (i.e., without internal channels). Alternatively, device 1 may include a microprotrusion layer 19 that has a combination of both boreless microprotrusions and bore-containing microprotrusions. The ingredient(s) in reservoir 18 may flow through these bores or channels in the microprotrusions, or may flow around and between solid microprotrusions when device 1 is in use. The microprotrusion layer 19 may also be any shape, including, but not limited to any geometric shape or, preferably, a ring-shape having an opening 19c in the center thereof. The microprotrusions themselves may be any shape. The base layer 19a is preferably formed of a flexible material but also can be of rigid material. The device of the present invention may be applied to areas of a patient's skin or mucosa that require the base layer 19a be flexible. The base layer 19a of microprotrusion layer 19 preferably is from about 1 mil to about 10 mils thick, more preferably from about 2 mils to about 8 mils thick and most preferably from about 4 mils to 6 mils thick. The microprotrusions 19b of microprotrusion layer 19 preferably project from base layer 19a a length of from about 20 to about 500 microns, more preferably from about 50 to about 400 microns and most preferably from about 100 to about 250 microns. However, the microprotrusions may be longer (e.g., 500-1000 microns or more) depending on the particular application.

Channeled Surface Flow Layer

The microprotrusion base layer 19a includes a surface 19f (FIG. 6) adjacent at least a portion of the adhesive layer 11, which optionally includes corrugations or channels 19e to direct the flow of ingredient(s) from reservoir 18. Alternatively, if the microprotrusion layer side 19f that is adjacent the adhesive layer 11 is substantially smooth (i.e., non-corrugated/non-channeled) the adhesive layer side adjacent the substantially smooth microprotrusion layer side 19f may include a pattern coated adhesive to create corrugations or channels to direct the flow of ingredient(s) between the substantially smooth microprotrusion layer side and the adhesive layer 11. When the above-noted corrugations or channels are present, either in microprotrusion base layer 19a or in the pattern coated adhesive, active ingredient(s) flow from reservoir 18 through the openings in cover 14, and adhesive layer 11 and at least a portion of the ingredient(s) are channeled to flow laterally between adhesive layer 11 and microprotrusion base layer 19a. The ingredient(s) then flow down through openings in the microprotrusions 19b, or through openings in base layer 19a, and then down around and between microprotrusions 19a, and then into and through the stratum corneum layer of the skin.

Microprotrusion Composition

The microprotrusion layer 19 may be comprised of any materials, including, but not limited to, thermoforming polymer materials that are synthetically and/or naturally derived. For example, suitable biocompatible, biodegradable polymers include poly(lactide)s, poly(glycolide)s, poly(lactide-co-glycolide)s, polyanhydrides, polyorthoesters, polyetheresters, polycaprolactones, polyesteramides, poly(butyric acid), poly(valeric acid), polyurethanes and copolymers and blends thereof. Representative non-biodegradable polymers include polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof. Other potential materials include metals including pharmaceutical grade stainless steel, gold, titanium, nickel, iron, tin, chromium, copper palladium, platinum and alloys of these and/or other metals. Additionally, glass, ceramics, epoxides or any combination or derivation of any of the above may be utilized, however, the preferred material is a polyamide such as nylon.

Release Liner Layer

Release liner 12 also preferably is comprised of a plurality of layers of material as follows: release coating layer 26 made of, for example, LOPAREX® (REXAM®) 92A release coating; barrier layer 28 made of, for example, 3.0 mil, PET film; adhesive layer 30, made of, for example, 1.0 mil NATIONAL STARCH 80-1197™ acrylic adhesive; and outer protective layer 32, which is a co-laminated film of polyamide and polyolefins layer, made of, for example, TOLAS™ 4050. These layers that comprise release liner 12 may be modified in thickness to accommodate the length of the microprotrusions and to provide adequate protection of the microprotrusions during storage and transportation. For example, if the microprotrusions are longer, then the thickness of the layers that comprise release liner 12 will be thicker. Conversely, if the microprotrusions are shorter in length, the layers that comprise release liner 12 will be thinner.

A release coating layer 26 is bonded to barrier layer 28. Adhesive layer 30 is bonded to the other side of barrier layer 28, and to outer protective layer 32. This entire assembly of layers functions as a unitary release liner.

Release coating layer 26, barrier layer 28 and adhesive layer 30 preferably have openings 26a, 28a and 30a, respectively, which are coextensive with the outer perimeter of microprotrusion layer 19 or, when present, the outer perimeter of one or more matrix active rings. In other words, layers 26, 28 and 30 of release liner 12 may partially overlay, or not overlay at all, cover 14 leaving sealing surface 14a and opening 15 exposed. Outer protective layer 32, on the other hand, has no such opening and entirely covers sealing surface 14a and opening 15 of cover 14. Thus it is preferably the exposed inner surface portion 32a of outer protective layer 32 which is sealed to sealing surface 14a of cover 14 by the previously referred to second seal 21 which is not subject to degradation, permeation or solubilization by any ingredient to be contained in reservoir 18. Outer protective layer 32 may be shaped such that it extends upwardly into openings 26a, 28a and 30a.

While those skilled in the art can select various adhesives for the first seal 17 and second seal 21 which would not be degradable by the particular ingredients to be contained in reservoir 18, the first seal 17 and second seal 21 are preferably heat seals. Thus, cover 14 is preferably heat sealed to backing layer 10 in the area thereof surrounding reservoir 18, and outer layer 32 of release liner 12 is preferably heat sealed in area 32A to sealing surface 14A. The materials and sealing conditions used to seal area 32A to sealing surface 14A are preferably such that this second seal 21 is "releasable" when force is applied to remove release liner 12 from adhesive composite 11. In contrast, the first seal 17 between cover 14 and backing layer 10 should be "permanent" to the extent that cover 14 is not peeled away from backing layer 10 when a force is applied to remove release liner 12 from the assembly.

Delivery of Active Ingredients

Preferred embodiment device 1 delivers active ingredients at high concentrations over short periods of time (i.e. ranging from about 0.1 hour to about 24 hours per wear). Some active ingredients at lower concentrations may be delivered for more than about 24 hours. The preferred embodiment device 1 is useful for delivering active ingredients in liquid solution without adding or incorporating an adhesive film (i.e. with no layer between the skin and the liquid containing the active ingredient) into the preferred embodiment device 1. Preferred embodiment device 1 may be used to treat the following conditions or to deliver the following active ingredients, the conditions and active ingredients including, but not limited to: warts (i.e. salicylic acid, and/or other keratolytic agents); acne (i.e. salicylic acid, benzoyl peroxide, antibiotics, and/or other keratolytic agents); pain (i.e. local anesthetics, non-steroidal anti-inflammatory drugs); moisturizers (i.e. urea, water); finger and toenail beds (i.e. urea, water, anti-fungal agents); skin buffering (i.e. buffering agents); vaccines (i.e. small pox, measles, flu, anthrax, polio, etc.); poorly soluble drugs; larger molecular weight molecules (i.e. about 500 to about 1500 molecular weight molecules such as heparin, LHRH); larger macromolecules (i.e., DNA, antibodies, growth factors, Factor VIII) vaccines; wound care (i.e. water, debriding agent(s), enzymes); sampling and diagnostic agents (i.e. glucose, lactic acid, potassium, allergens, etc.); iontophoresis, electroporation, sonophoresis, radio frequency, thermal enhancement (reservoir) (i.e. electrode (anode, cathode)); microneedles (reservoir) (i.e. alone or in combination with iontophoresis, electroporation, sonophoresis, radio frequency, thermal enhancement). The preferred embodiment device 1 may also be combined with other components, deliver other active ingredients, and/or deliver molecule(s) for diagnostic purposes to the skin.

Description of Layers

The following is a description of the array of layers in device 1, from the backing layer 10 to the release liner 12 (top to bottom on FIG. 2) by layer number and description:

10. Backing layer, i.e. 3.0 mil, 3M® 9722 polyethylene film;
18. Reservoir ingredients, i.e. 5.0 mil STRATEX® 90% polypropylene/10% non-woven rayon;
14. Cover or retaining ring, i.e. 4.0 mil ROLLPOINT® polyethylene film;
11. Adhesive layer
    20. First adhesive coating, i.e. 1.0 mil National Starch 80-1197 acrylic adhesive
    22. Barrier layer, i.e. 0.5 mil PET film; and
    24. Second adhesive coating, i.e. 3.0 mil National Starch 80-1197 acrylic adhesive;
19. Microprotrusion layer, i.e., a polyamide such as nylon;
12. Release liner;
    26. Release coating layer, i.e. LOPAREX® (REXAM®) 92A release coating;
    28. Barrier layer, i.e. 3.0 mil PET film;
    30. Adhesive coating, i.e. 1.0 mil NATIONAL STARCH 80-1197™; and
    32. Outer protective layer, i.e. TOLAS™ 4050;

Any commercially known method of manufacturing the preferred embodiment device 1 may be employed. However, one preferred method of producing device 1 includes the following steps: 1) pre-cut the materials used in the backing 10 and the reservoir overlying portion 16 (i.e., pre-cut cover 14 and any woven and/or non-woven ingredients); 2) peel away the strip layers from first adhesive layer 20 and second adhesive layer 24 and adhere the skin contact adhesive layer 11 to at least a portion of microprotrusion layer 19 and to at least a portion of the release liner 12; 3) place cover 14 in position on completed step 2 assembly, heat seal cover 14 to the outer protective layer 32 and set aside; 4) form reservoir overlying portion 16 in the backing material; 5) place ingredients 18 in the formed reservoir, insert any active ingredient(s), place completed step 3 assembly in position over reservoir 16 and heat seal backing 10 to cover 14; 6) die cut finished shape; 7) inspect for defects and contamination; and 8) place the finished device 1 in a pouch and seal the pouch.

In use, the release liner 12 is removed from the microprotrusion transdermal delivery device 1 thereby breaking second seal 21 between the release liner 12 and sealing surface 14A of cover 14, exposing the microprotrusion layer side containing the microprotrusions and/or microneedles and exposing at least a portion of adhesive layer 11. The microprotrusion transdermal delivery device 1 is then applied to a subject's skin or mucosa. During application, the microprotrusions and/or microneedles pierce the stratum corneum layer of the skin or epithelial cells of the mucosa creating perforations in the skin or mucosa and are depressed to a desired depth. The ingredients contained within reservoir 16 flow through the one or more openings in cover 14 and contact the skin or mucosa. At least a portion of the adhesive layer 11 contacts the skin or mucosa and forms an adhesive seal creating the outer boundary of a second reservoir. Upon contacting the skin or mucosa, the ingredients from the reservoir seep through the perforations created in the skin or mucosa by the microprotrusions and/or microneedles. Alternatively, ingredients from reservoir 18 may pass through opening 15 in cover 14 and, while a portion of ingredients may directly seep into the skin through the perforations as described above, a separate portion of the ingredients may be channeled, via the channels in the microprotrusion layer side adjacent adhesive layer 11, through the optional bores within the microprotrusion and/or microneedles and be delivered through the stratum corneum layer of the skin. Alternatively, if the microprotrusion layer side adjacent the adhesive layer is substantially smooth, the channels may be created by a pattern coat adhesive. During the application and ingredient delivery process, the second reservoir contains the ingredients.

Force Gauge Indicator

Another embodiment of the microprotrusion transdermal delivery device of the present invention includes device 50 (FIG. 3). Device 50 is identical to device 1 as described above, but further includes force gauge 34. Force gauge 34 may be structurally incorporated into backing layer 10 or shell 2 or may be a separate attachment wherein backing layer 10 is adapted to receive force gauge 34. Force gauge 34 includes an indicator such as an audio, visual or otherwise sensory indicator.

The application of microprotrusion transdermal delivery device 50 is substantially similar to the application process described above, however, pressure is applied to force gauge 34 to depress the microneedles and/or microprotrusions to the desired depth in a subject's skin. Upon applying an adequate amount of pressure to depress the microprotrusion and/or microneedles in the stratum corneum, the sensory indicator is activated (i.e., changes color, changes shape, makes a noise, etc.), which informs the person applying the device that the microprotrusions and/or microneedles are properly depressed in the patient's skin.

Force gauge 34 may be comprised of any material, including, but not limited to all of the microprotrusion materials previously disclosed, plastics, rubbers or any combination or derivation of any of the above. Force gauge 34 may be any shape as long as the shape is capable of being, or of being connected to, a sensory indicator. The illustrated force gauge 34 is the form of a dimple or dome that collapses upon application of a known, predetermined force. The force gauge 34 may generate an audible click sound as it collapses. The magnitude of the force being applied by a user also decreases abruptly as it collapses. The drop in force and/or click provide feedback to the user, thereby indicating that the proper amount of force has been used.

Secondary Active Matrix

Referring to FIG. 4 in yet another embodiment, the microprotrusion transdermal delivery device 100 includes substantially the same components as device 1 described in the preferred embodiment (see FIG. 2), but further includes one or more matrix active ring(s) 36. The matrix active ring(s) 36 are disposed between adhesive layer 11 and release liner 12. The matrix active ring(s) 36 may contain any active and/or non-active ingredients, including, but not limited to, immediate-acting active ingredients, controlled, sustained, or otherwise prolonged active ingredients, any non-active ingredients, and/or ingredients that are incompatible with the ingredients contained within reservoir 18 of the device 1. The matrix active ring(s) 36 may be comprised of any material, including, but not limited to a gel matrix which incorporates the ingredient to be dispensed, or an absorbent material which absorbs active ingredients and releases them. It can also comprise an adhesive matrix which incorporates ingredients to be dispensed into the matrix. The overall thickness of the matrix active ring(s) 36 are relatively thin.

Optionally, microprotrusion layer 19 may also be included in this embodiment. When microprotrusion layer 19 is utilized in this embodiment, ingredient(s) 18 flow from reservoir 16 through the opening 15 in cover 14, and adhesive layer 11 and at least a portion of the ingredient(s) from reservoir 18 are channeled to flow laterally between adhesive layer 11 and microprotrusion layer 19. The ingredient(s) then flow down through the openings in the microneedles into and through the stratum corneum layer of the skin. When both matrix active ring(s) 36 and microprotrusion layer 19 are utilized in the device of this embodiment, matrix active ring(s) 36 are adjacent adhesive layer 11 and distal from the at least one opening in microprotrusion layer 19.

Microprotrusion Recoil Layer

Figure 6:
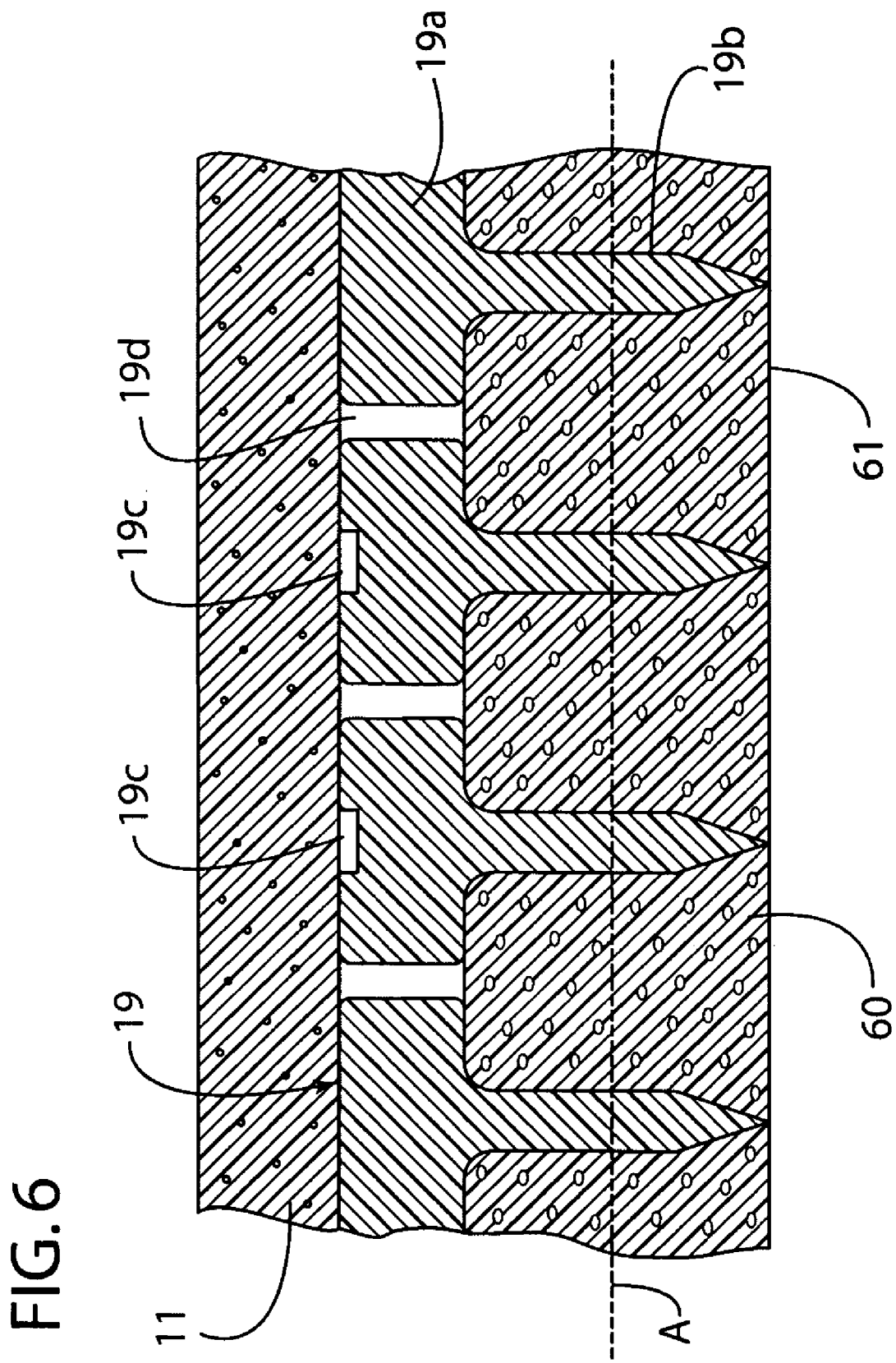
FIG. 6 is a fragmentary, cross-sectional view of a microprotrusion member and recoil device.

With reference to FIG. 6, the transdermal delivery device may include a recoil device such as a thin layer of compressible/resilient foam 60. In use, a user applies a force to the microprotrusion member 19 to push the microneedles 19b into the skin. As the microneedles 19b enter the skin, the foam layer 60 is compressed such that surface 61 shifts as indicated by the line "A". Upon release of a force by a user, the foam 60 generates a force tending to pull the microneedles 196 out of the skin, thereby providing a recoil device.

Figure 7:
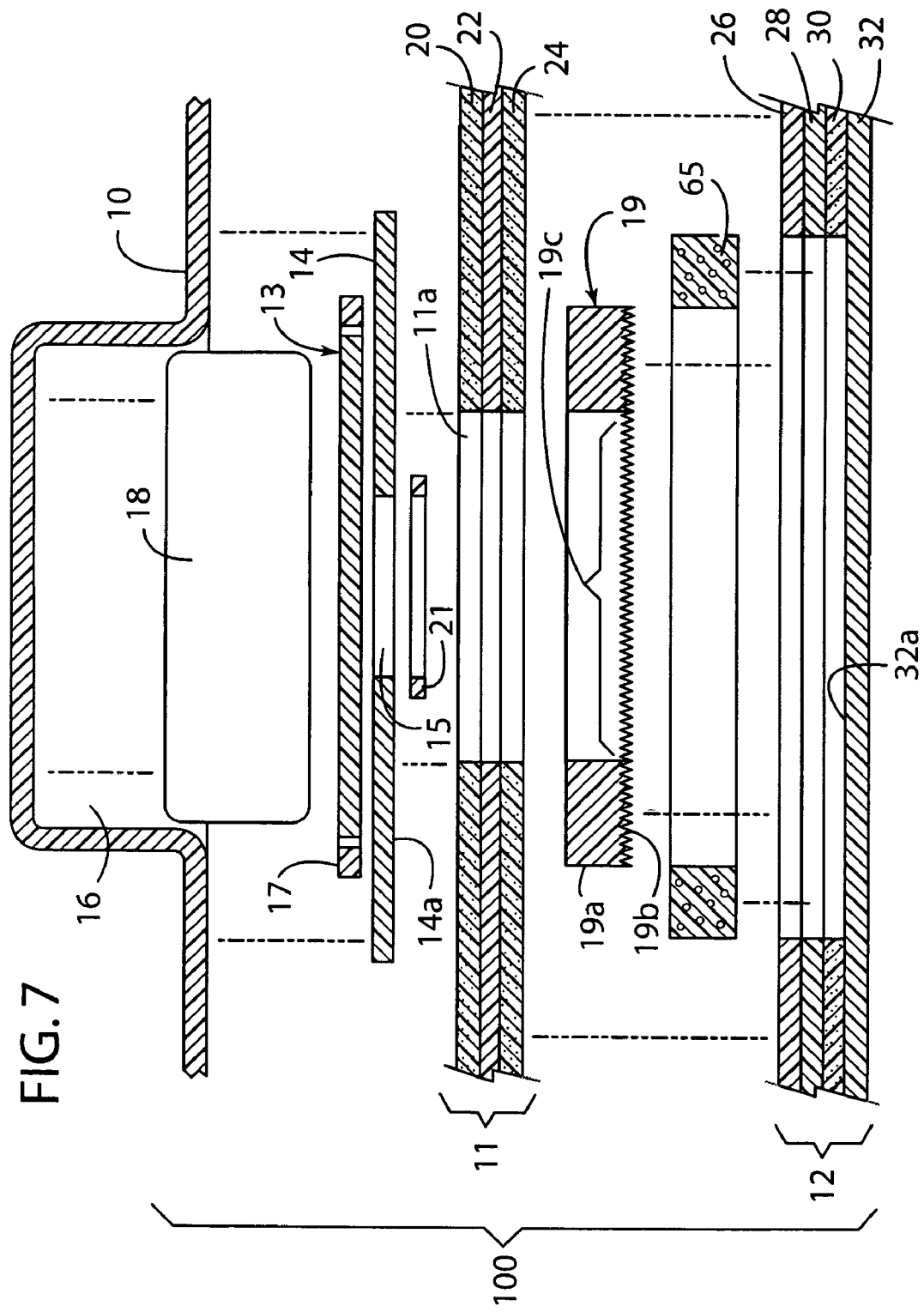
FIG. 7 is an exploded cross-sectional view of the principle subassemblies of the device including a recoil device according to another aspect of the present invention.

With further reference to FIG. 7, a ring 65 of resilient material may also be utilized to provide a recoil device. As illustrated in FIG. 7, the resilient ring 65 may have a shape and location that is substantially the same as active ring 36. The resilient ring 65 may be adhered to barrier layer 22 via adhesive 24. Alternately, resilient ring 65 could extend around the outside of an active ring 36 in a concentric manner (not shown).

The microprotrusion layer 19 shown in FIG. 6 includes a plurality of openings 19d therethrough to provide for flow of ingredients from reservoir 18 through microprotrusion layer 19. As discussed above, openings through hollow microneedles could also be utilized.

Microprotrusion Protector Spacers

Figure 8:
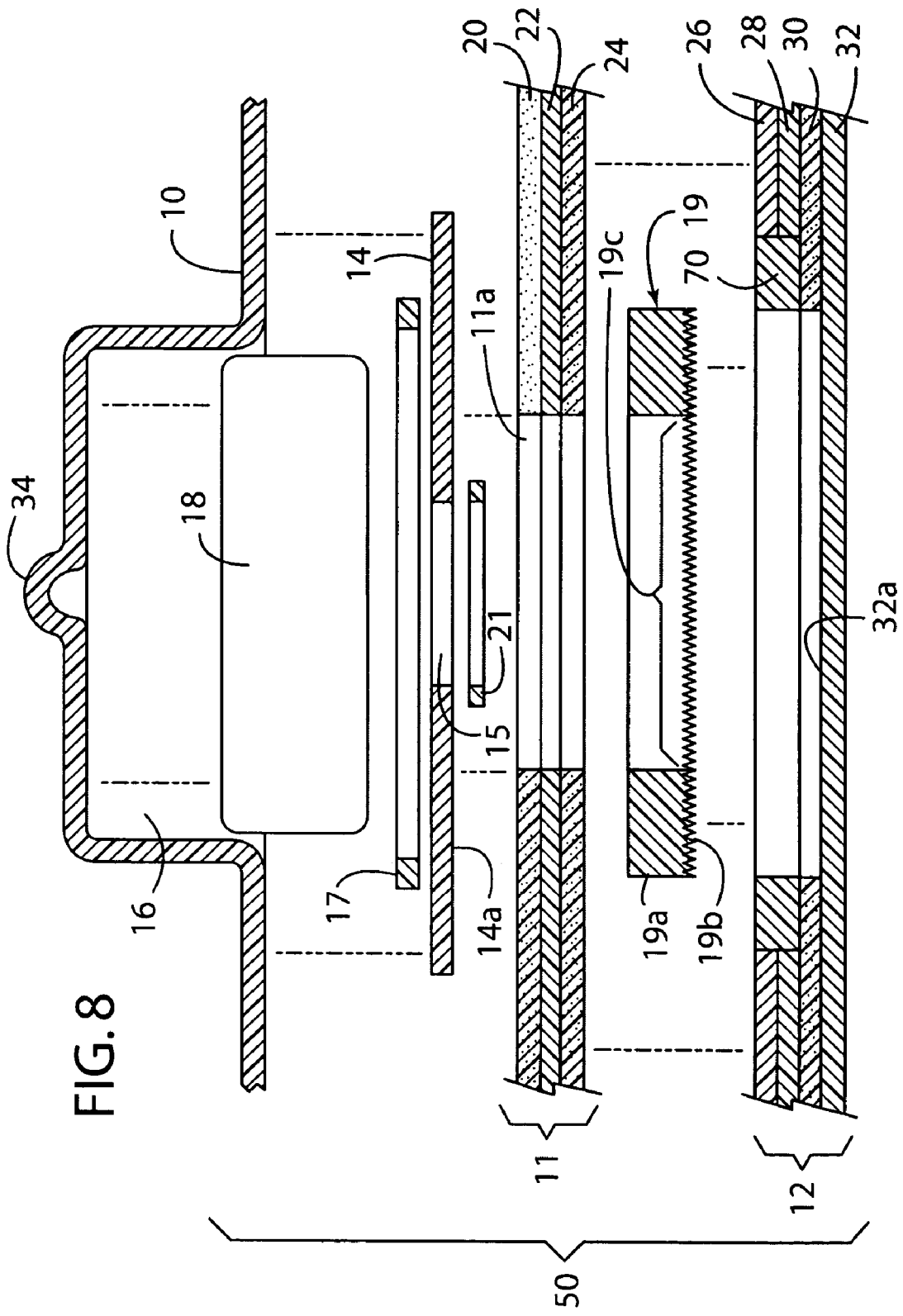
FIG. 8 is an exploded cross-sectional view of the principle subassemblies of the device including a bumper guard according to another aspect of the present invention.

As illustrated in FIG. 8, a bumper guard such as a ring 70 may be adhered to the liner 12. Ring 70 is made of a material that is substantially incompressible, such as a suitable polymer material, and prevents damage to microneedles 19b in the event outer protective layer 32 is bumped or the like during shipping storage and the like. In use, the ring 70 is removed with liner 12 immediately prior to application of device 1. It will be readily appreciated that a bumper guard could have a variety of configurations. For example, the bumper guard could have the shape of a shallow cup or cap, including a sheet of relatively rigid material (not shown) formed integrally with ring 70 and extending over microneedles 19b to further protect microneedles 196.

Additional Separate Ingredient Compartments

Figure 9:
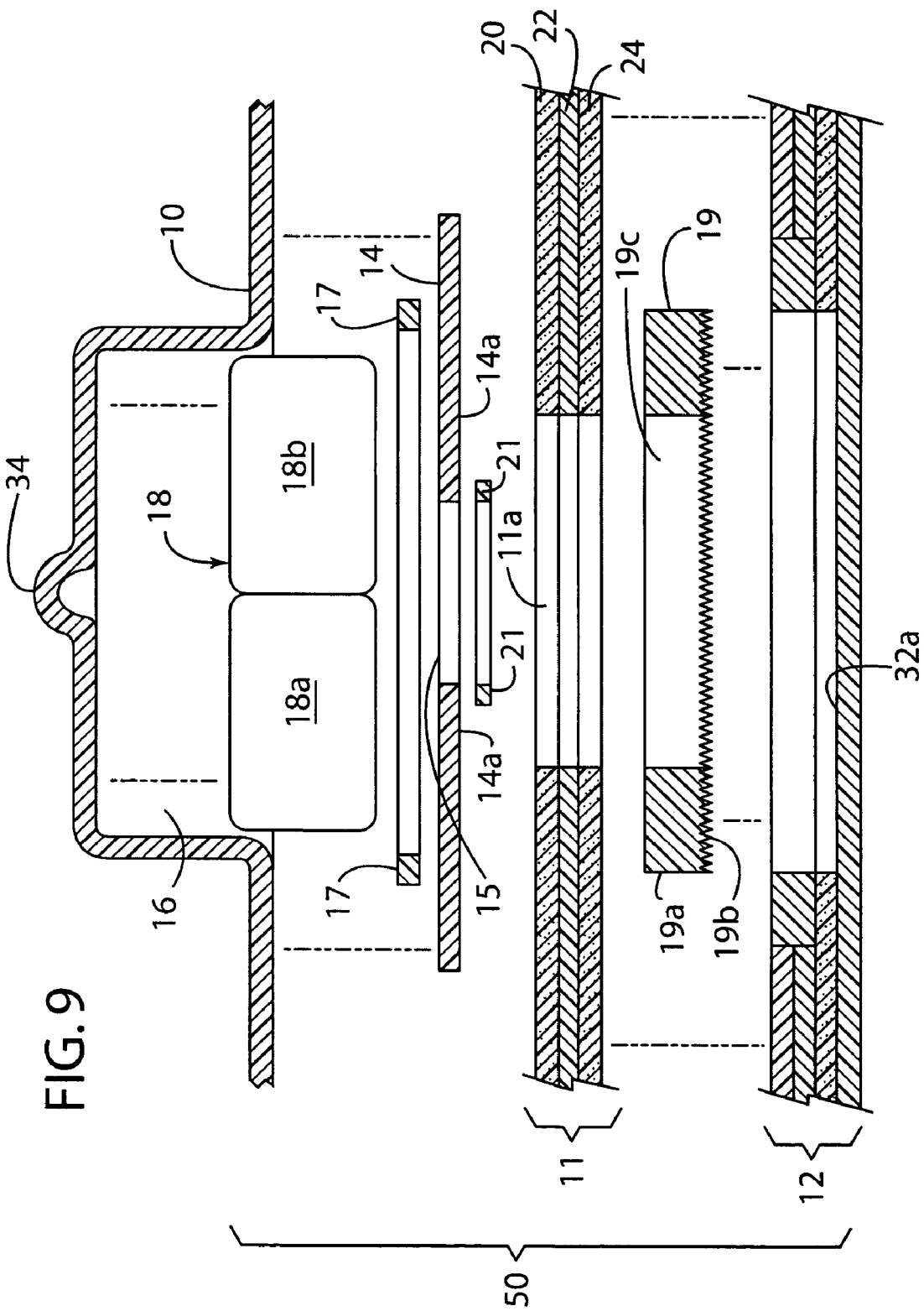
FIG. 9 is an exploded cross-sectional view of the principle subassemblies of the device including a reservoir having a plurality of discreet chambers according to another aspect of the present invention.

With further reference to FIG. 9, reservoir 18 could include multiple separate compartments 18a, 18b that hold two or more different ingredients. It will be appreciated that the reservoir compartments 18a and 18b may be completely sealed off by cover 14 and backing layer 10. The multiple compartments may be utilized for different ingredients that are not compatible with one another or the like.

Having described specific preferred embodiments of the invention with reference to the accompanying drawings, it will be appreciated that the present invention is not limited to those precise embodiments and that various changes and modifications can be effected herein by one of ordinary skill in the art without departing from the scope or spirit of the invention as defined by the appended claims.

The invention claimed is:

1. A microprotrusion transdermal delivery device, comprising:
   an ingredient-containing reservoir defining a perimeter;
   a backing member overlying the ingredient containing reservoir, said backing member being made of a material which is substantially impermeable to ingredients contained in the reservoir;
   a cover for the reservoir, the cover being made of a material substantially impermeable to ingredients contained in the reservoir, but having at least one opening defining a perimeter, such that ingredients to be delivered from the reservoir will flow through the opening, but will not readily flow through the material of which the cover is made;
   a first seal sealing the cover to the backing member at the perimeter of the reservoir wherein the first seal which is not subject to permeation, disintegration or degradation by any ingredient contained in the reservoir;
   an adhesive layer adhered to the backing member for adhering the device to a patient's skin or mucosa, the adhesive layer not extending to the perimeter of the opening in the cover, such that a portion of the cover surrounding the perimeter of the opening is exposed to thereby define a cover sealing surface;
   a microprotrusion layer at least partially adhered to the adhesive layer, the microprotrusion layer including at least one opening therethrough generally aligned with the opening in the cover, such that ingredients to be delivered from the reservoir flow through the opening in the microprotrusion layer, wherein the microprotrusion layer pierces at least a portion of the skin or mucosa when the device is applied to a subject's skin or mucosa;
   a second seal;
   a liner covering the cover sealing surface and the opening in the cover, the liner being releasably sealed to the cover sealing surface by the second seal, wherein the second seal is not subject to permeation, disintegration or degradation by any ingredient in the reservoir;
   whereby ingredients contained in the reservoir are sealed therein during storage and non-use by the first and second seals, but are free to flow through the openings in the microprotrusion layer and the cover and onto a subject's skin or mucosa when the liner is removed from the device and the device is applied to skin or mucosa.

2. The device of claim 1 in which the adhesive layer overlies at least a portion of the cover.

3. The device of claim 2, wherein the liner is a release liner for the device, the release liner covering the microprotrusion layer, the adhesive layer, the sealing surface, and the opening of the cover.

4. The device of claim 3, wherein the first and second seals comprise heat seals between the cover and the backing member and between the liner and the cover respectively.

5. The device of claim 3, wherein the liner is a composite member comprising:
an outer protective layer and a barrier layer and an adhesive coating therebetween, and wherein
the barrier layer has an exposed surface with a release coating on the exposed surface; and wherein the barrier layer has an opening therein which is sufficiently large to expose the opening and the sealing surface of the cover, whereby the outer protective layer is sealed directly to the sealing surface of the cover by the second seal.

6. The device of claim 5, wherein the adhesive layer is a composite member comprising:
a first adhesive coating, a second adhesive coating and a barrier layer therebetween; and wherein
the barrier layer has an opening therein which is sufficiently large to expose the opening and the sealing surface of the cover, whereby the outer protective layer is sealed directly to the sealing surface of the cover by the second seal.

7. The device of claim 6, wherein the second adhesive coating adjacent the microprotrusion layer comprises a pattern-coated adhesive.

8. The device of claim 6, wherein the release coating of the liner is releasably adhered to at least a portion of the second adhesive coating of the adhesive layer.

9. The device of claim 3, wherein the microprotrusion layer comprises a base layer having microprotrusions projecting therefrom.

10. The device of claim 9, wherein the microprotrusion layer includes a channeled surface in the base layer, adjacent to the adhesive layer to provide flow of the ingredients from the reservoir.

11. The device of claim 1, wherein the ingredients contained in the reservoir comprise a liquid.

12. The device of claim 1, wherein the reservoir comprises an absorbable material.

13. The device of claim 1, wherein the ingredients contained in the reservoir comprise a gel.

14. The device of claim 1, including a rate controlling membrane disposed between the cover and said reservoir.

15. The device of claim 1, including a rate controlling membrane disposed between the cover and the adhesive layer.

16. The device of claim 1, wherein the microprotrusion layer includes a channeled surface in the base layer, adjacent to the adhesive layer, to provide flow of ingredients from the reservoir.

17. The device of claim 1, wherein the backing member overlies the ingredient containing reservoir, the backing member including a force gauge, wherein the force gauge includes an indicator which indicates when an adequate amount of pressure has been applied to depress the microprotrusion layer in a patient's skin.

18. The device of claim 17 in which the adhesive layer overlies at least a portion of the cover.

19. The device of claim 18, wherein the liner is a release liner for the device, the release liner substantially covering the microprotrusion layer, the adhesive layer, the sealing surface, and the opening of the cover.

20. The device of claim 19, wherein the first and second seals are heat seals between the cover and the backing member and between the liner and the cover respectively.

21. The device of claim 19, wherein the liner is a composite member comprising:
an outer protective layer and a barrier layer having an exposed surface, the liner further including an adhesive coating between the outer protective layer and the barrier layer, and a release coating on the exposed surface of the barrier layer; and wherein
the barrier layer has an opening therein which is sufficiently large to expose the opening and the sealing surface of the cover, whereby the outer protective layer is sealed directly to the sealing surface of the cover by the second seal.

22. The device of claim 21, wherein the adhesive layer is a composite member comprising:
a first adhesive coating, a second adhesive coating and a barrier layer therebetween; and wherein
the barrier layer, including its first adhesive coating and its second adhesive coating, has an opening therein which is sufficiently large to expose the opening and the sealing surface of the cover, whereby the outer protective layer is sealed directly to the sealing surface of the cover by the second seal.

23. The device of claim 22, wherein the release coating of the liner is releasably adhered to at least a portion of the second adhesive coating of the adhesive layer.

* * * * *

UNITED STATES PATENT AND TRADEMARK OFFICE
CERTIFICATE OF CORRECTION

PATENT NO.       : 7,611,481 B2                           Page 1 of 1
APPLICATION NO.  : 11/088829
DATED            : November 3, 2009
INVENTOR(S)      : Cleary et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 670 days.

Signed and Sealed this

Twelfth Day of October, 2010

David J. Kappos
*Director of the United States Patent and Trademark Office*